United States Patent [19]

Chrubasik et al.

[11] Patent Number: 4,670,418

[45] Date of Patent: Jun. 2, 1987

[54] METHOD OF USING SOMATOSTATIN AS AN ANALGESIC OR AN ANESTHETIC

[75] Inventors: Joachim Chrubasik; Sigrun Chrubasik, both of Freiburg, Fed. Rep. of Germany

[73] Assignee: CuraMED Pharma GmbH, Freiburg, Fed. Rep. of Germany

[21] Appl. No.: 709,549

[22] Filed: Mar. 8, 1985

[30] Foreign Application Priority Data

Mar. 13, 1984 [DE] Fed. Rep. of Germany ....... 3409062
Oct. 30, 1984 [DE] Fed. Rep. of Germany ....... 3439716

[51] Int. Cl.$^4$ ............................................. G01N 31/00
[52] U.S. Cl. ....................................... 514/11; 514/806
[58] Field of Search ..................... 260/112.55; 514/11, 514/806

*Primary Examiner*—Delbert R. Phillips
*Attorney, Agent, or Firm*—Wegner & Bretschneider

[57] ABSTRACT

Somatostatin in the form of a peridural, intraspinal or intraventricular injection and/or infusion can be used as an analgesic or anesthetic.

8 Claims, No Drawings

METHOD OF USING SOMATOSTATIN AS AN ANALGESIC OR AN ANESTHETIC

BACKGROUND OF THE INVENTION

The present invention relates to a new use of somatostatin.

DESCRIPTION OF THE PRIOR ART

Somatostatin is a synthetic peptide which has so far been used to treat gastroduodenal ulcus hemorrhages, serious acute hemorrhages in those cases of acute erosive or hemorrhagic gastritis, and for the prophylaxis of post-operative pancreatic complications following pancreas surgery. Somatostatin inhibits the release of growth hormones and other hormones such as TSH, insulin, glucagon, gastrin, secretin, and cholecystokinine. There has further been described by M. Rezek at al., Can. J. Physiol. Pharmacol. 56, 227–231 (1977) that, after an intracerebroventricular infusion of somatostatin in rats, a short-term analgesic effect was found. The half-life of somatostatin (2 to 4 minutes) is extremely short. However, in human medicine, a intracerebroventricular permanent infusion is not practicable.

GENERAL DESCRIPTION OF THE INVENTION

It has now been found surprisingly that somatostatin, upon peridural application, is capable of rapidly (and to a high degree) penetrating the dura whereafter it gets into the liquor. Thus, somatostatin is able to reach the opiate receptors and there to develop a surprisingly beneficial and previously unknown analgesic activity. It further has been found that intraspinal and even intraventricular somatostatin injections and infusions show a marked analgesic effect, comparable to that of morphine, in humans. Cancer patients suffering from intolerable pain in the final stage of post-operative pain were given 250 µg of somatostatin as an injection and thereafter 10 to 50 µg/hour of somatostatin as an infusion, in part via the intraspinal route and in part via the intraventricular route. These treatments resulted in a marked analgesia, comparable to that of morphine. The infusions were tolerated without any occurring side-effects for a period of over two weeks.

It further has been found that intradural or intraspinal somatostatin injections or infusions have anesthetic effects and, thus, can be employed in the place of conventional anesthetics.

Thus, absolutely new and highly interesting fields of applications are opening for somatostatin, all the more so as the other effects and side-effects have been well investigated.

SUMMARY OF THE INVENTION

It is an object of the present invention to provide a new use of somatostatin in the form of peridural, intraspinal or intraventricular injections as an analgesic or an intradural or an intraspinal anesthetic.

It is another object of the present invention to provide the use of somatostatin for preparing peridural, intraspinal or intraventricular injection solutions as an analgesic or an anesthetic.

DETAILED DESCRIPTION OF THE INVENTION

A peridural, intraspinal, or intraventricular injection solution can be formulated using previously known solutions for injection and infusion. It is also possible to use solutions that which are available in the form of isotonic sterile pyrogern-free sodium chloride solution. The quantity of somatostatin in the solution can vary depending upon the intended use.

Because of the short half-life time of somatostatin, the application form has to be adapted. For this purpose, there are suitable, for example, externally attachable small metering devices adapted to allow the administration of a permanent infusion. In the intraventricular application, an artificial orifice is prepared in the skull to provide access to the ventricle, and the infusion solution is introduced thereby.

Upon an investigation with dogs, it has been determined that the analgesic activity will be maintained for several weeks. The analgesia test according to Cohen (J. Surg. 32, 32–37 (1982)) resulted in the finding that all of the animals tolerated a heated plate of 60° C. for a period of 5 seconds. A dog having a large decubitus showed no signs of pain. Moreover, the dogs had not been put under sedation and showed a balanced behavior. No side effects were apparent.

Preliminary experiments with humans have confirmed that a peridural application of 125 µg and of 250 µg, respectively, of somatostatin, is analgesically effective.

In spite of the good compatibility, the amounts of somatostatin as respectively applied will be kept as low as possible. Some results imply that dosage can be chosen at a smaller level than that previously used.

What is claimed is:

1. A method of producing an analgesic effect in a human patient in need thereof comprising
   injecting or infusing said patient with a solution containing an analgetically effective amount of somatostatin.
2. The method of claim 1 wherein said solution is administered peridurally.
3. The method of claim 1 wherein said solution is administered intraspinally.
4. The method of claim 1 wherein said solution is administered intraventricularly.
5. The method of claim 1 wherein somatostatin is administered in a quantity of about 125 µg to about 250 µg.
6. A method of producing an anesthetic effect in a patient in need thereof comprising
   injecting or infusing said patient with a solution containing an anesthetically effective amount of somatostatin.
7. The method of claim 6 wherein said solution is administered intradurally.
8. The method of claim 6 wherein said solution is administered intraspinally.

* * * * *